(12) United States Patent
Dunican et al.

(10) Patent No.: US 6,586,214 B1
(45) Date of Patent: Jul. 1, 2003

(54) METHOD FOR INCREASING THE METABOLIC FLUX THROUGH THE PENTOSE PHOSPHATE CYCLE IN CORYNEFORM BACTERIA BY REGULATION OF THE PHOSPHOGLUCOSE ISOMERASE (PGI GENE)

(75) Inventors: L. K. Dunican, Galway (IE); Ashling McCormack, Athlone (IE); Cliona Stapleton, Roscrea (IE); Kevin Burke, Galway (IE); Michael O'Donohue, Tralee (IE); Achim Marx, Bielefeld (DE); Bettina Mockel, Bielefeld (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/396,478

(22) Filed: Sep. 15, 1999

(51) Int. Cl.$^7$ ............................. C12N 9/90; C12N 1/20; C12P 13/04; C12P 19/30; C12P 1/00
(52) U.S. Cl. ................. 435/115; 435/252.32; 435/106; 435/89; 435/41; 435/233; 435/477; 435/487; 536/23.2
(58) Field of Search ............................. 435/41, 89, 106, 435/233, 252.32, 115, 477, 487; 536/23.2

(56) References Cited

U.S. PATENT DOCUMENTS 5,605,818 A * 2/1997 Katsumata et al. ......... 435/108

FOREIGN PATENT DOCUMENTS

| EP | 1 108 790 | 6/2001 |
| WO | WO 01/00844 | 1/2001 |
| WO | WO 01/07626 | 2/2001 |

OTHER PUBLICATIONS

Mascarenhas et al., Appl. Environ. Microbiol. 57(10):2995–2999, 1991.*
Malin & Bourd, Journal of Applied Bacteriology 71, p. 517–523, 1991.
Shio et al., Agricultural and Biological Chemistry 54, p. 1513–1519, 1990.
Yamamoto et al., Journal of Fermentation Technology 64, p. 285–291, 1986.
Oishi & Aida (Agricultural and Biological Chemistry 29, p. 83–89, 1965.
Ishono et al., Journal of General and Applied Microbiology 37, p. 157–165, 1991 Gene und Clone, Eine Einführung in die 6. Gentechnologie (Verlag Chemie, Weinheim, Germany 1990).
Kohara et al., Cell 50, p. 495–508, 1987.
Bathe et al., Molecular and General Genetics, 252, p. 255–265, 1996.
Wahl et al., 1987, Proceedings of the National Academy of Sciences, USA 84, p. 2160–2164.
Raleigh et al., 1988, Nucleic Acids Research 16 p. 1563–1575.
Börmann et al., Molecular Microbiology 6(3), p. 317–326, 1992.
Hohn & Collins, Gene 111, p. 291–298, 1980.
Vieira et al., 1982, Gene, 19 p. 259–268.
Tauch et al., 1994, FEMS Microbiological Letters, 123 p. 343–347.
Sanger et al., Proceedings of the National Academy of Sciences of USA, 74: p. 5463–5467, 1977.
Nucleic Acids Research 14, p. 217–232, 1986.
Methods of Biochemical Analysis 39, p. 74–97, 1998.
Proceedings of the National Academy of Sciences of USA 85, p. 2444–2448, 1988.
Altschul et al., Nature Genetics 6, p. 119–129, 1994.
Liebl et al., International Journal of Systematic Bacteriology, 1991, 41 p. 255–260.
Sonntag et al., Applied Microbiology and Biotechnology 44, p. 489–495, 1995.
Marx et al., Biotechnology and Bioengineering 49, p. 111–129 1996.
Marx et al., Biotechnology and Bioengineering 56, p. 168–180 1997.
Journal of Bacteriology 162, p. 591–597 1985.
Short et al., Nucleic Acids Research 16, p. 7583–7600, 1988.
Suginoto et al., Bioscience, Biotechnology and Biochemistry, vol. 61, 1997 (10) p. 1760–1762.

* cited by examiner

Primary Examiner—Rebecca E. Prouty
(74) Attorney, Agent, or Firm—Pillsbury Winthrop, LLP (57) ABSTRACT

The present invention is directed to isolated polynucleotides coding for phosphoglucose isomerase (pgi) from coryneform bacteria. In addition, the invention includes methods for increasing the metabolic flux through pentose phosphate cycle of bacteria by reducing or eliminating the activity of pgi. These methods may be used to increase the fermentative production of nucleotides, vitamins and amino acids.

8 Claims, 2 Drawing Sheets

METHOD FOR INCREASING THE METABOLIC FLUX THROUGH THE PENTOSE PHOSPHATE CYCLE IN CORYNEFORM BACTERIA BY REGULATION OF THE PHOSPHOGLUCOSE ISOMERASE (PGI GENE)

BACKGROUND OF THE INVENTION

1. Field of the Invention

The present invention provides nucleotide sequences from coryneform bacteria coding for the pgi gene and a process for increasing metabolic flux through the pentose phosphate cycle by attenuating the pgi gene.

2. Background Information

Nucleotides, vitamins and in particular L-amino acids, very particularly lysine and tryptophan, are used in the foodstuffs industry, in animal nutrition, human medicine and the pharmaceuticals industry.

It is known that these substances are produced by fermentation using strains of coryneform bacteria, in particular *Corynebacterium glutamicum*. Due to its great significance, efforts are constantly being made to improve the production process. Improvements to the process may relate to measures concerning fermentation technology, for example stirring and oxygen supply, or to the composition of the nutrient media, such as for example sugar concentration during fermentation, or to working up of the product by, for example, ion exchange chromatography, or to the intrinsic performance characteristics of the microorganism itself.

The performance characteristics of these microorganisms are improved using methods of mutagenesis, selection and mutant selection. In this manner, strains are obtained which are resistant to antimetabolites or are auxotrophic for regulatorily significant intermediates and produce nucleotides, vitamins or amino acids.

For some years, methods of recombinant DNA technology have also been used to improve strains of Corynebacterium which produce nucleotides, vitamins and L-amino acids.

A typical raw material for the production of these compounds is glucose, which is usually used in the form of starch hydrolysate. Sucrose is also used as a raw material.

On cellular absorption, glucose is phosphorylated with consumption of phosphoenolpyruvate (phosphotransferase system) (Malin & Bourd, Journal of Applied Bacteriology 71, 517–523 (1991)) and is then available to the cell as glucose-6-phosphate. Sucrose is converted into fructose and glucose-6-phosphate by a phosphotransferase system (Shio et al., Agricultural and Biological Chemistry 54, 1513–1519 (1990)) and invertase reaction (Yamamoto et al., Journal of Fermentation Technology 64, 285–291 (1986)).

During glucose catabolism, the enzymes glucose-6-phosphate dehydrogenase (EC 1.1.14.9) and glucose-6-phosphate isomerase (EC 5.3.1.9) compete for the substrate glucose-6-phosphate. The enzyme glucose-6-phosphate isomerase catalyses the first reaction step of the Embden-Meyerhof-Parnas pathway or glycolysis, namely conversion into fructose-6-phosphate. The enzyme glucose-6-phosphate dehydrogenase catalyses the first reaction step of the oxidative portion of the pentose phosphate cycle, namely conversion into 6-phosphogluconolactone.

In the oxidative portion of the pentose phosphate cycle, glucose-6-phosphate is converted into ribulose-5-phosphate, so producing reduction equivalents in the form of NADPH. As the pentose phosphate cycle proceeds further, pentose phosphates, hexose phosphates and triose phosphates are interconverted. Pentose phosphates, such as for example 5-phosphoribosyl-1-pyrophosphate are required, for example, in nucleotide biosynthesis. 5-Phosphoribosyl-1-pyrophosphate is moreover a precursor for aromatic amino acids and the amino acid L-histidine. NADPH acts as a reduction equivalent in numerous anabolic biosyntheses. Four molecules of NADPH are thus consumed for the biosynthesis of one molecule of L-lysine from oxalacetic acid.

The significance of the pentose phosphate cycle to biosynthesis and the production of amino acids, in particular L-lysine, by coryneform bacteria is known and has been the focus of much special interest.

Oishi & Aida (Agricultural and Biological Chemistry 29, 83–89 (1965)) have accordingly reported the "hexose monophosphate shunt" of *Brevibacterium ammoniagenes*. Investigations using $^{13}C$ isotope methods by Ishino et al. (Journal of General and Applied Microbiology 37, 157–165 (1991)) into glucose metabolism during glutamic acid and lysine fermentation indicate a correlation between lysine production and metabolic flux through the pentose phosphate pathway.

SUMMARY OF THE INVENTION

Object of the Invention

The inventors set themselves the object of providing a process for increasing metabolic flux through the pentose phosphate cycle.

Description of the Invention

Nucleotides, vitamins and in particular L-amino acids, very particularly L-lysine and L-tryptophan, are used in the foodstuffs industry, in animal nutrition, human medicine and the pharmaceuticals industry. There is accordingly general interest in providing improved processes for the production of these products.

The present invention provides an isolated polynucleotide containing a polynucleotide sequence selected from the group a) polynucleotide which is at least 70% identical to a polynucleotide which codes for a polypeptide containing the amino acid sequence of SEQ ID no. 2, b) polynucleotide which codes for a polypeptide which contains an amino acid sequence which is at least 70% identical to the amino acid sequence of SEQ ID no. 2, c) polynucleotide which is complementary to the polynucleotides of a) or b), and d) polynucleotide containing at least 100 successive bases of the polynucleotide sequence of a), b) or c).

The present invention also provides the polynucleotide as claimed in claim 1, wherein it preferably comprises replicable DNA containing:

(i) the nucleotide sequence shown in SEQ ID no. 1 or (ii) at least one sequence which matches the sequence (i) within the degeneration range of the genetic code, or (iii) at least one sequence which hybridises with the complementary sequence to sequence (i) or (ii) and optionally (iv) functionally neutral sense mutations in (i).

The present invention also provides a polynucleotide as claimed in claim 2, containing the nucleotide sequence as shown in SEQ ID no. 1, a polynucleotide as claimed in claim 2 which codes for a polypeptide which contains the amino acid sequence as shown in SEQ ID no. 2, a vector containing the polynucleotide as claimed in claim 1, indent d, in particular pMC1, deposited in *E. coli* DSM 12969.

and coryneform bacteria acting as host cells which contain the vector as claimed in claim 6.

"Isolated" means separated from its natural environment. "Polynucleotide" generally relates to polyribonucleotides and polydeoxyribonucleotides, wherein the RNA or DNA may be unmodified or modified.

"Polypeptides" are taken to mean peptides or proteins which contain two or more amino acids connected by peptide bonds.

The polypeptides according to the invention include the polypeptide according to SEQ ID no. 2, in particular those having the biological activity of glucose-6-phosphate isomerase and also those which are at least 70% identical to the polypeptide according to SEQ ID no. 2, preferably being at least 80% and particularly preferably at least 90% to 95% identical to the polypeptide according to SEQ ID no. 2 and having the stated activity.

This invention furthermore relates to a process for the fermentative production of nucleotides, vitamins and in particular L-amino acids, very particularly lysine and tryptophan, using coryneform bacteria which in particular already produce the stated substances and in which the nucleotide sequences coding for the pgi gene are attenuated, in particular expressed at a low level.

In this connection, the term "attenuation" describes the reduction in or switching off of the intracellular activity of one or more enzymes (proteins) in a microorganism, which enzymes are coded by the corresponding DNA, for example by using a weak promoter or a gene or allele which codes for a corresponding enzyme having low activity or inactivates the corresponding enzyme (protein) and optionally by combining these measures.

The microorganisms provided by the present invention are capable of producing nucleotides, vitamins and in particular L-amino acids, very particularly lysine and tryptophan, from glucose, sucrose, lactose, fructose, maltose, molasses, starch, cellulose or from glycerol and ethanol. The microorganisms may comprise representatives of the coryneform bacteria in particular of the genus Corynebacterium. Within the genus Corynebacterium, Corynebacterium glutamicum may in particular be mentioned, which is known in specialist circles for its ability to produce L-amino acids.

Suitable strains of the genus Corynebacterium, in particular of the species *Corynebacterium glutamicum*, are the known wild type strains

*Corynebacterium glutamicum* ATCC13032

*Corynebacterium acetoglutamicum* ATCC15806

*Corynebacterium acetoacidophilum* ATCC13870

*Corynebacterium thermoaminogenes* FERM BP-1539

*Brevibacterium flavum* ATCC14067

*Brevibacterium lactofermentum* ATCC13869 and

*Brevibacterium divaricatum* ATCC14020 and mutants or strains produced therefrom which produce nucleotides, vitamins or L-amino acids, such as for example the 5'-inosinic acid producing strains

*Corynebacterium ammoniagenes* ATCC15190

*Corynebacterium ammoniagenes* ATCC15454 and

*Corynebacterium glutamicum* ATCC14998 or such as for example the 5'-guanylic acid producing strains

*Corynebacterium glutamicum* ATCC21171 and

*Corynebacterium ammoniagenes* ATCC19216 or such as for example the D-pantothenic acid producing strains

*Corynebacterium glutamicum*

ATCC13032/pECM3ilvBNCD, pEKEX2panBC and

*Corynebacterium glutamicum* ATCC13032/pND-D2 or such as for example the L-lysine producing strains

*Corynebacterium glutamicum* FERM-P 1709

*Brevibacterium flavum* FERM-P 1708

*Brevibacterium lactofermentum* FERM-P 1712

*Corynebacterium glutamicum* FERM-P 6463

*Corynebacterium glutamicum* FERM-P 6464 and

*Corynebacterium glutamicum* DSM 5714 or such as for example the L-tryptophan producing strains

*Corynebacterium glutamicum* ATCC21850 and

*Corynebacterium glutamicum* KY9218(pKW9901).

The inventors were successful in isolating the novel pgi gene coding for the enzyme glucose-6-phosphate isomerase (EC 5.3.1.9) from *C. glutamicum*.

In order to isolate the pgi gene or also other genes from *C. glutamicum*, a gene library of this microorganism is first constructed in *E. coli*. The construction of gene libraries is described in generally known textbooks and manuals. Examples which may be mentioned are the textbook by Winnacker: Gene und Klone, Eine Einführung in die Gentechnologie (Verlag Chemie, Weinheim, Germany, 1990) or the manual by Sambrook et al.: Molecular Cloning, A Laboratory Manual (Cold Spring Harbor Laboratory Press, 1989). One very well known gene library is that of *E. coli* K-12 strain W3110, which was constructed by Kohara et al. (Cell 50, 495–508 (1987)) in λ-vectors. Bathe et al. (Molecular and General Genetics, 252:255–265, 1996) describe a gene library of *C. glutamicum* ATCC13032, which was constructed using the cosmid vector SuperCos I (Wahl et al., 1987, Proceedings of the National Academy of Sciences USA, 84:2160–2164) in *E. coli* K-12 strain NM554 (Raleigh et al., 1988, Nucleic Acids Research 16:1563–1575). Börmann et al. (Molecular Microbiology 6(3), 317–326)) again describe a gene library of *C. glutamicum* ATCC13032 using cosmid pHC79 (Hohn & Collins, Gene 11, 291–298 (1980)). O'Donohue (The Cloning and Molecular Analysis of Four Common Aromatic Amino Acid Biosynthetic Genes from *Corynebacterium glutamicum*. Ph.D. Thesis, National University of Ireland, Galway, 1997) describes the cloning of *C. glutamicum* genes using the λ Zap Expression system described by Short et al. (Nucleic Acids Research, 16: 7583).

A gene library of *C. glutamicum* in *E. coli* may also be produced using plasmids such as pBR322 (Bolivar, Life Sciences, 25, 807–818 (1979)) or pUC9 (Vieira et al., 1982, Gene, 19:259–268). Suitable hosts are in particular those *E. coli* strains with restriction and recombination defects, such as for example strain DH5α ((Jeffrey H. Miller: "A Short Course in Bacterial Genetics, A Laboratory Manual and Handbook for *Escherichia coli* and Related Bacteria", Cold Spring Harbor Laboratory Press, 1992).

Figure 1:
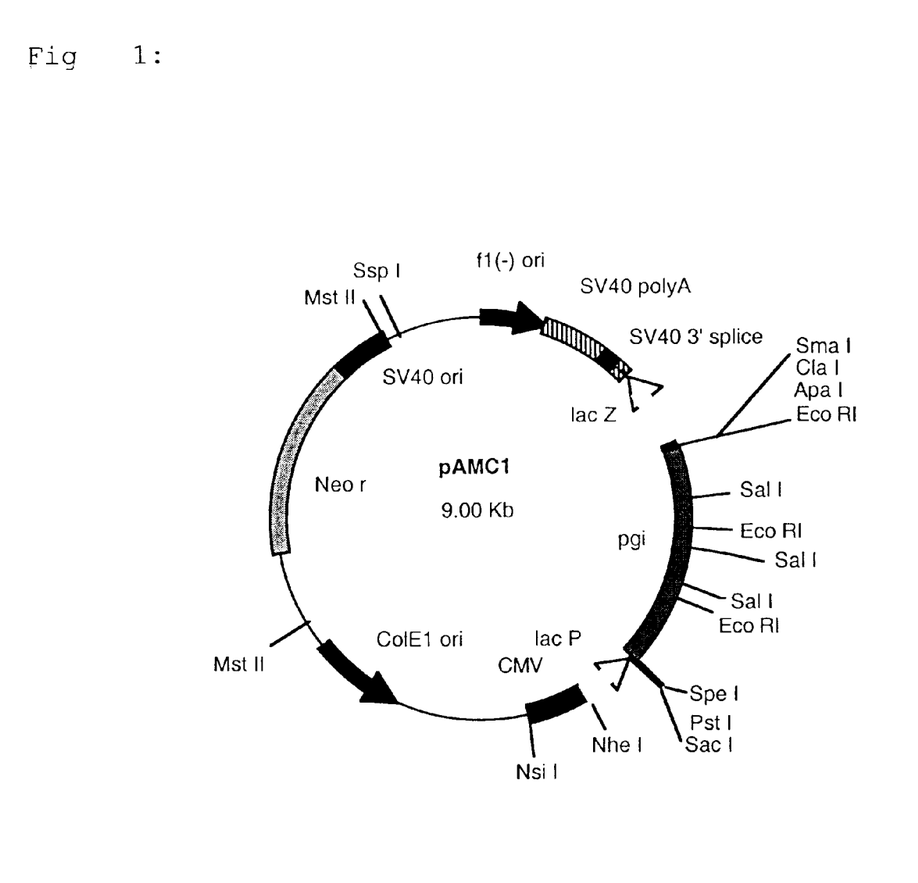
FIG. 1: Map of plasmid pAMC1.

The gene library is then inserted into an indicator strain by transformation (Hanahan, Journal of Molecular Biology 166, 557–580, 1983) or electroporation (Tauch et.al., 1994, FEMS Microbiological Letters, 123:343–347). The indicator strain is distinguished by having a mutation in the gene in question which causes a detectable phenotype. The *E. coli* mutant DF1311 described by Kupor & Fraenkel (Journal of Bacteriology 100: 1296–1301 (1969)) is of significance for the purposes of the present invention. This strain carries mutations in the pgi and pgl genes, as a result of which growth on glucose is severely inhibited. After transformation with a vector containing the pgi gene, growth on glucose is re-established. One example of such a vector containing the pgi gene is pAMC1 (FIG. 1).

The long DNA fragments cloned with the assistance of cosmids or other λ-vectors may subsequently in turn be sub-cloned in usual vectors suitable for DNA sequencing.

DNA sequencing methods are described inter alia in Sanger et al. (Proceedings of the National Academy of Sciences of the United States of America USA, 74:5463–5467, 1977).

The resultant DNA sequences may then be investigated using known algorithms or sequence analysis programs, for example Staden's program (Nucleic Acids Research 14, 217–232(1986)), Butler's GCG program (Methods of Biochemical Analysis 39, 74–97 (1998)), Pearson & Lipman's FASTA algorithm (Proceedings of the National Academy of Sciences USA 85,2444–2448 (1988)) or Altschul et al.'s BLAST algorithm (Nature Genetics 6, 119–129 (1994)) and compared with the sequence entries available in publicly accessible databases. Publicly accessible nucleotide sequence databases are, for example, the European Molecular Biology Laboratory database (EMBL, Heidelberg, Germany) or the National Center for Biotechnology Information database (NCBI, Bethesda, Md., USA).

These were the methods used to obtain the novel DNA sequence coding for the pgi gene from *C. glutamicum*, which is provided by the present invention as SEQ ID no. 1. The amino acid sequence of the corresponding protein was furthermore deduced from the above DNA sequence using the methods described above. SEQ ID no. 2 shows the resultant amino acid sequence of the product of the pgi gene.

Coding DNA sequences arising from SEQ ID NO.1 by the degeneracy of the genetic code are also provided by the present invention. Similarly, DNA sequences which hybridise with SEQ ID no. 1 or portions of SEQ ID no. 1 are also provided by the present invention. Finally, DNA sequences produced by the polymerase chain reaction (PCR) using primers obtained from SEQ ID no. 1 are also provided by the present invention.

The person skilled in the art may find instructions for identifying DNA sequences by means of hybridisation inter alia in the manual "The DIG System Users Guide for Filter Hybridization" from Boehringer Mannheim GmbH (Mannheim, Germany, 1993) and in Liebl et al. (International Journal of Systematic Bacteriology (1991) 41: 255–260). The person skilled in the art may find instructions for amplifying DNA sequences using the polymerase chain reaction (PCR) inter alia in the manual by Gait: Oligonucleotide synthesis: a practical approach (IRL Press, Oxford, UK, 1984) and in Newton & Graham: PCR (Spektrum Akademischer Verlag, Heidelberg, Germany, 1994).

The inventors discovered that, after attenuation of the pgi gene, coryneform bacteria exhibit an improved metabolic flux through the pentose phosphate cycle and produce nucleotides, vitamins and in particular L-amino acids, particularly preferably L-lysine and L-tryptophan, in an improved manner.

Attenuation may be achieved by reducing or switching off either the expression of the pgi gene or the catalytic properties of the enzyme protein. Both measures may optionally be combined.

Reduced gene expression may be achieved by appropriate control of the culture or by genetic modification (mutation) of the signal structures for gene expression. Signal structures for gene expression are, for example, repressor genes, activator genes, operators, promoters, attenuators, ribosome binding sites, the start codon and terminators. The person skilled in the art will find information in this connection for example in patent application WO 96/15246, in Boyd & Murphy (Journal of Bacteriology 170: 5949 (1988)), in Voskuil & Chambliss (Nucleic Acids Research 26: 3548 (1998), in Jensen & Hammer (Biotechnology and Bioengineering 58: 191 (1998)), in Patek et al. (Microbiology 142: 1297 (1996) and in known textbooks of genetics and molecular biology, such as for example the textbook by Knippers ("Molekulare Genetik", 6th edition, Georg Thieme Verlag, Stuttgart, Germany, 1995) or by Winnacker ("Gene und Klone", VCH Verlagsgesellschaft, Weinheim, Germany, 1990).

Mutations which result in modification or reduction of the catalytic properties of enzyme proteins are known from the prior art; examples which may be mentioned are the papers by Qiu & Goodman (Journal of Biological Chemistry 272: 8611–8617 (1997)), Sugimoto et al. (Bioscience Biotechnology and Biochemistry 61: 1760–1762 (1997)) and M öckel ("Die Threonindehydratase aus *Corynebacterium glutamicum*: Aufhebung der allosterischen Regulation und Struktur des Enzyms", Forschungszentrum Jülich reports, J ül-2906, ISSN09442952, Jülich, Germany, 1994). Summary presentations may be found in known textbooks of genetics and molecular biology such as, for example, the textbook by Hagemann ("Allgemeine Genetik", Gustav Fischer Verlag, Stuttgart, 1986).

Mutations which may be considered are transitions, insertions, deletions and transversions Depending upon the effect of exchanging the amino acids upon enzyme activity, the mutations are known as missense mutations or nonsense mutations. Insertions or deletions of at least one base pair in a gene give rise to frame shift mutations, as a result of which the incorrect amino acids are inserted or translation terminates prematurely. Deletions of two or more codons typically result in a complete breakdown of enzyme activity. Instructions for producing such mutations belong to the prior art and may be found in known textbooks of genetics and molecular biology, such as for example the textbook by Knippers ("Molekulare Genetik", 6th edition, Georg Thieme Verlag, Stuttgart, Germany, 1995), by Winnacker ("Gene und Klone", VCH Verlagsgesellschaft, Weinheim, Germany, 1990) or by Hagemann ("Allgemeine Genetik", Gustav Fischer Verlag, Stuttgart, 1986).

One example of insertion mutagenesis is plasmid pMC1 (FIG. 2), by means of which the pgi gene may be mutated. Plasmid pMC1 consists of plasmid pBGS8, described by Spratt et al. (Gene 41: 337 (1986)), into which an internal fragment of the pgi gene, shown in SEQ ID no. 3, has been inserted. After transformation and homologous recombination into the pgi gene (insertion), this plasmid brings about a complete loss of enzyme function. Instructions and explanations relating to insertion mutagenesis may be found, for example, in Schwarzer & Pühler (Bio/Technology 9, 84–87 (1991)) or Fitzpatrick et al. (Applied Microbiology and Biotechnology 42, 575–580 (1994)).

In addition to attenuation of the pgi gene, it may additionally be advantageous for the production of nucleotides, vitamins and in particular L-amino acids, very particularly L-lysine and L-tryptophan, to amplify, in particular overexpress, one or more enzymes of the particular biosynthetic pathway.

For example, when producing nucleotides, it is thus possible
- simultaneously to overexpress the purF gene coding for glutamine-PRPP amidotransferase and/or
- simultaneously to overexpress the carAB gene coding for carbamoylphosphate synthetase.

For example, when producing L-lysine, it is thus possible
- simultaneously to overexpress the dapA gene coding for dihydrodipicolinate synthase (EP-B 0 197 335), and/or
- simultaneously to amplify a DNA fragment which imparts S-(2-aminoethyl)cysteine resistance (EP-A 0 088 166).

For example, when producing L-tryptophan, it is thus possible
- simultaneously to overexpress the tkt gene coding for transketolase and/or
- simultaneously to overexpress the prs gene coding for phosphoribosylpyrophosphate synthase.

Apart from attenuating the pgi gene, it may furthermore be advantageous for the production of nucleotides, vitamins and in particular L-amino acids, very particularly L-lysine and L-tryptophan, to switch off unwanted secondary reactions (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms containing the polynucleotide as claimed in claim 1 are also provided by the invention and may be cultured continuously or discontinuously using the batch process or the fed batch process or repeated fed batch process for the purpose of producing nucleotides, vitamins and in particular L-amino acids, very particularly L-lysine and L-tryptophan. A summary of known culture methods is given in the textbook by Chmiel (Bioprozesstechnik 1. Einf uhrung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must adequately satisfy the requirements of the particular strains. Culture media for various microorganisms are described in "Manual of Methods for General Bacteriology" from American Society for Bacteriology (Washington D.C., USA, 1981). Carbon sources which may be used include sugars and carbohydrates, such as for example glucose, sucrose, lactose, fructose, maltose, molasses, starch and cellulose, oils and fats, such as for example soya oil, sunflower oil, peanut oil and coconut oil, fatty acids, such as for example palmitic acid, stearic acid and linoleic acid, alcohols, such as for example glycerol and ethanol, and organic acids, such as for example acetic acid. These substances may be used individually or as a mixture. Nitrogen sources which may be used comprise organic compounds containing nitrogen, such as peptones, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture. Phosphorus sources which may be used are phosphoric acid, potassium dihydrogen phosphate or dipotassium hydrogen phosphate or the corresponding salts containing sodium. The culture medium must furthermore contain metal salts, such as for example magnesium sulfate or iron sulfate, which are necessary for growth. Finally, essential growth-promoting substances such as amino acids and vitamins may also be used in addition to the above-stated substances. Suitable precursors may furthermore be added to the culture medium. The stated feed substances may be added to the culture as a single batch or be fed appropriately during cultivation.

Basic compounds, such as sodium hydroxide, potassium hydroxide, ammonia or ammonia water, or acidic compounds, such as phosphoric acid or sulfuric acid, are used appropriately to control the pH of the culture. Antifoaming agents, such as for example fatty acid polyglycol esters, may be used to control foaming. Suitable selectively acting substances, such as for example antibiotics, may be added to the medium in order to maintain plasmid stability. Oxygen or gas mixtures containing oxygen, such as for example air, are introduced into the culture in order to maintain aerobic conditions. The temperature of the culture is normally from 20° C. to 45° C. and preferably from 25° C. to 40° C. The culture is continued until a maximum quantity of the desired product has been formed. This objective is normally achieved within 10 hours to 160 hours.

Metabolic flux through the pentose phosphate cycle is determined by using a culture containing C-1 labelled 13C glucose as the carbon source. This analytical method is based on the known fact that when glucose is catabolised by the pentose phosphate cycle, the C-1 position is converted into carbon dioxide, whereas when it is catabolised by glycolysis, the 13C-1 labelling is passed on to the C-3 position of the pyruvate. The 13C content of the C-3 position of the pyruvate is determined at the appropriate time by using nuclear magnetic resonance or mass spectroscopy methods to investigate extracellular metabolites, such as for example lactate and in particular lysine. Alternatively, amino acids may be obtained by acid hydrolysis from the biomass and the 13C content in the individual carbon atoms of the particular amino acid may then be determined. The person skilled in the art may find comprehensive instructions, in particular in relation to computer-aided data evaluation of the 13C content in various carbon atoms of the investigated metabolites in Sonntag et al. (European Journal of Biochemistry 213, 1325–1331 (1993)), Sonntag et al. (Applied Microbiology and Biotechnology 44, 489–495 (1995)), Marx et al. (Biotechnology and Bioengineering 49, 111–129 (1996)) and Marx et al. (Biotechnology and Bioengineering 56, 168–180 (1997)).

Methods for determining nucleotides, vitamins and L-amino acids are known from the prior art. L-Amino acids may, for example, be analysed using anion exchange chromatography with subsequent ninhydrin derivatisation, as described by Spackman et al. (Analytical Chemistry, 30, (1958), 1190), or they may be analysed by reversed phase HPLC as described in Lindroth et al. (Analytical Chemistry (1979) 51: 1167–1174).

The following microorganism has been deposited with Deutschen Sammlung für Mikrorganismen und Zellkulturen (DSMZ, Braunschweig, [sic] The following microorganism has been deposited with Deutschen Sammlung für Mikrorganismen und Zellkulturen (DSMZ, Braunschweig, Germany) in accordance with the Budapest Treaty:

*Escherichia coli* strain DH5α/pMC1 as DSM 22969

DETAILED DESCRIPTION OF THE INVENTION

The following examples will further illustrate this invention. The molecular biology techniques, e.g. plasmid DNA isolation, restriction enzyme treatment, ligations, standard transformations of *Escherichia coli* etc. used are, (unless stated otherwise), described by Sambrook et al., (Molecular Cloning. A Laboratory Manual (1989) Cold Spring Harbor Laboratories, USA).

EXAMPLE 1

Construction of a Gene Library of *Corynebacterium glutamicum* Strain AS019

A DNA library of *Corynebacterium glutamicum* strain ASO19 (Yoshihama et al., Journal of Bacteriology 162, 591–597 (1985)) was constructed using λ Zap Express™ system, (Short et al., (1988) Nucleic Acids Research, 16: 7583–7600), as described by O'Donohue (O'Donohue, M. (1997). The Cloning and Molecular Analysis of Four Common Aromatic Amino Acid Biosynthetic Genes from *Corynebacterium glutamicum*. Ph.D. Thesis, National University of Ireland, Galway). λ Zap Express™ kit was purchased from Stratagene (Stratagene, 11011 North Torrey Pines Rd., La Jolla, Calif. 92037) and used according to the manufacturer's instructions. AS019-DNA was digested with restriction enzyme Sau3A and ligated to BamHI treated and dephosphorylated λ Zap Express™ arms.

EXAMPLE 2

Cloning and Sequencing of the pgi Gene

1. Cloning

*Escherichia coli* strain DF1311, carrying mutations in the pgi and pgl genes as described by Kupor & Fraenkel, (Journal of Bacteriology 100: 1296–1301 (1969)), was transformed with approx. 500 ng of the AS019 λ Zap Express™ plasmid library described in Example 1. Selection for transformants was made on M9 minimal media, (Sambrook et al., (1989). Molecular Cloning. A Laboratory Manual Cold Spring Harbor Laboratories, USA), containing kanamycin at a concentration of 50 mg/l and incubation at 37° C. for 48 hours. Plasmid DNA was isolated from one transformant according to Birnboim & Doly (Nucleic Acids Research 7: 1513–1523 (1979)) and designated pAMC1 (FIG. 1).

2. Sequencing

For sequence analysis of the cloned insert of pAMC1 the method of Sanger et al. (Proceedings of the National Academy of Sciences USA 74, 5463–5467 (1977)) was applied using primers differentially labelled with a coloured fluorescent tag. It was carried out using the ABI prism 310 genetic analyser from Perkin Elmer Applied Biosystems, (Perkin Elmer Corporation, Norwalk, Conn., U.S.A), and the ABI prism Big Dye™ Terminator Cycle Sequencing Ready Reaction kit also from Perkin Elmer.

Initial sequence analysis was carried out using the universal forward and M13 reverse primers obtained from Pharnacia Biotech (St. Albans, Herts, AL1 3AW UK):

Universal forward primer: GTA ATA CGA CTC ACT ATA GGG C (SEQ ID NO:4)

M13 reverse primer: GGA AAC AGC TAT GAC CAT G (SEQ ID NO:5) Internal primers were subsequently designed from the sequence obtained which allowed the entire pgi gene to be deduced. The sequence of the internal primers is as follows:

Internal primer 1: GGA AAC AGG GGA GCC GTC (SEQ ID NO:6)

Internal primer 2: TGC TGA GAT ACC AGC GGT (SEQ ID NO:7)

Sequence obtained was then analysed using the DNA Strider program (Marck, (1988)). Nucleic Acids Research 16: 1829–1836), version 1.0 on an Apple Macintosh computer. This program allowed for analyses such as restriction site usage, open reading frame analysis and codon usage determination. Searches between DNA sequence obtained and those in EMBL and Genbank databases were achieved using the BLAST program, (Altschul et al., (1997). Nucleic Acids Research, 25: 3389–3402). DNA and protein sequences were aligned using the Clustal V and Clustal W programs (Higgins and Sharp, 1988 Gene 73: 237–244).

The sequence thus obtained is shown in SEQ ID NO 1. The analysis of the nucleotide sequence obtained revealed an open reading frame of 1650 base pairs which was designated as pgi gene. It codes for a protein of 550 amino acids shown in SEQ ID NO 2.

EXAMPLE 3

Mutagenesis of the pgi Gene

1. Construction of a pgi disruption vector

An internal segment of the pgi gene was amplified by polymerase chain reaction (PCR) using genomic DNA isolated from *Corynebacterium glutamicum* ASO19, (Heery & Dunican, (1993) Applied and Environmental Microbiology 59: 791–799), as template. The pgi primers used were:

fwd. Primer: ATG GAR WCC AAY GGH AA (SEQ ID NO:8)

rev. Primer: YTC CAC GCC CCA YTG RTC (SEQ ID NO:9)

with R=A+G; Y=C+T; W=A+T; H=A+T+C.

PCR Parameters were as follows:

35 cycles

94° C. for 1 min.

47° C. for 1 min.

72° C. for 30 sec.

1.5 mM MgCl$_2$ approx. 150–200 ng DNA template.

Figure 2:
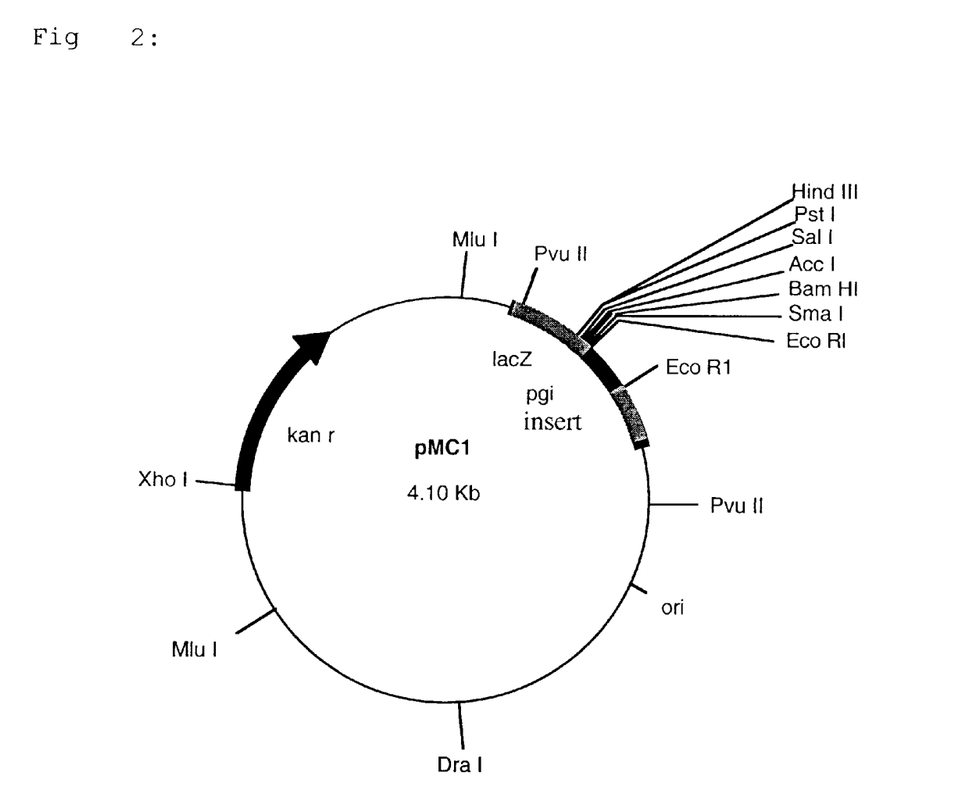
FIG. 2: Map of plasmid pMC1.

The PCR product obtained was cloned into the commercially available PGEM-T vector received from Promega Corp., (Promega UK, Southampton) using strain *E. coli* JM109, (Yanisch-Perron et al., 1985. Gene, 33: 103–119), as a host. The sequence of the PCR product is shown as SEQ ID No. 3. The cloned insert was then excised as an EcoRI fragment and ligated to plasmid pBGS8 (Spratt et al., Gene 41: 337–342 (1986)) pretreated with EcoRI. The restriction enzymes used were obtained from Boehringer Mannheim UK Ltd., (Bell Lane, Lewes, East Sussex BN7 1LG, UK) and used according to the manufacturer's instructions. *E. coli* JM109 was then transformed with this ligation mixture and electrotransformants were selected on Luria agar supplemented with IPTG (isopropyl-β-D-thiogalactopyranoside), XGAL (5-bromo-4-chloro-3-indolyl-D-galactopyranoside) and kanamycin at a concentration of 1 mM, 0.02% and 50 mg/l respectively. Agar plates were incubated for twelve hours at 37° C. Plasmid DNA was isolated from one transformant, characterised by restriction enzyme analysis using EcoRI, BamHI and SalI designated pMC1 (FIG. 2).

2. Insertion Mutagenesis of the pgi Gene in Strain DSM5715

Strain DSM 5715 was then transformed with plasmid pMC1 using the electroporation method described by Liebl et al. (FEMS Microbiology Letters, 53:299–303 (1989)).

Transformant selection proceeded on LBHIS agar consisting of 18.5 g/l of brain-heart infusion bouillon, 0.5 M sorbitol, 5 g/l of Bacto tryptone, 2.5 g/l of Bacto yeast extract, 5 g/l of NaCl and 18 g/l of Bacto agar, which had been supplemented with 15 mg/l of kanamycin and 1% fructose. Incubation was performed for 2 days at 33° C. Transformants 1, 2 and 3 were obtained.

The resultant transformants were were tested using the polymerase chain reaction (PCR). To this end, chromosomal DNA was isolated from the transformants obtained and from strain DSM5715 as described in Eikmanns et al. (Microbiology 140: 1817–1828 (1994)). The following primer oligonucleotides were selected for PCR on the basis of the DNA sequence of the pgi gene, which is shown in SEQ ID NO:1:

pgi-1: 5' ACC CAC GCT GTC CTA CCT TA 3' (SEQ ID NO:10)

pgi-2: 5' TGT CCC AAA TCA CGC CCT AG 3' (SEQ ID NO:11)

pgi-3: 5' gat gat agc ggc cag tgc at 3' (SEQ ID NO:12).

The primers shown were synthesised by the company MWG Biotech (Ebersberg, Germany) and the PCR reaction performed using the standard PCR method of Innis et al. (PCR-Protocols. A guide to methods and applications, 1990, Academic Press). The chromosomal DNA of the transformants was used as the template, and the chromosomal DNA of DSM5715 was used as the control. Each template was used in two PCR reactions, one with the primer pair pgi-1/pgi-2 and one with the primer pair pgi-1/pgi-3.

The PCR batches were separated by electrophoresis in a 0.8% agarose gel. Using primer pair pgi-1/pgi-2, each of the four PCR reactions yielded a DNA fragment of a length of 0.5 kb. Using primer pair pgi-1/pgi-3, only the control with DSM5715 DNA showed an amplification product of a length of 0.7 kb. No PCR product could be detected in the batches with chromosomal DNA from the transformants.

Transformant no. 3 characterised in this manner was named strain DSM5715:pMC1.

The abbreviations and names are defined as follows:

Neo r: Neomycin/kanamycin resistance

ColE1 ori: origin of replication of plasmid ColE1

CMV: Cytomegalovirus promoter lacP: lactose promoter pgi: phosphoglucose isomerase gene lacZ: 5'-end of β-galactosidase gene SV40 3' splice: 3' splice site of Simian Virus 40

SV40 polyA: polyadenylation site of Simian Virus 40 f1(–)ori: origin of replication of filamentous phage f1

SV40 ori: origin of replication of filamentous phage f1 kan r: kanamycin resistance pgi insert: internal fragment of gene pgi ori: origin of replication of plasmid pBGS8

AccI: cut site of restriction enzyme AccI

ApaI: cut site of restriction enzyme ApaI

BamHI: cut site of restriction enzyme BamHI

ClaI: cut site of restriction enzyme ClaI

DraI: cut site of restriction enzyme DraI

EcoRI: cut site of restriction enzyme EcoRI

HindIII: cut site of restriction enzyme HindIII

MluI: cut site of restriction enzyme MluI

MstII: cut site of restriction enzyme MstII

NheI: cut site of restriction enzyme NheI

NsiI: cut site of restriction enzyme NsiI

PstI: cut site of restriction enzyme PstI

PvuII: cut site of restriction enzyme PvuII

SacI: cut site of restriction enzyme SacI

SalI: cut site of restriction enzyme SalI

SmaI: cut site of restriction enzyme SmaI

SpeI: cut site of restriction enzyme SpeI

SspI: cut site of restriction enzyme SspI

---

What is claimed is:

1. A process for increasing the metabolic flux through the pentose phosphate cycle in coryneform bacteria, said process comprising:
 (a) eliminating the intracellular activity of a phosphoglucose isomerase (pgi) enzyme comprising the amino acid sequence of SEQ ID NO:2 in said coryneform bacteria; and
 (b) fermenting the coryneform bacteria of step (a), wherein elimination is achieved by one or more methods of mutagenesis selected from the group consisting of deletion mutagenesis with deletion of two or more codons in the pgi gene; insertional mutagenesis due to homologous recombination; and transition or transversion mutagenesis with incorporation of a non-sense mutation in the pgi gene.

2. A process for producing L-lysine using coryneform bacteria, said process comprising:
 (a) eliminating the intracellular activity of a phosphoglucose isomerase (pgi) enzyme comprising the amino acid sequence of SEQ ID NO:2 in said coryneform bacteria;
 (b) fermenting the coryneform bacteria of step (a);
 (c) allowing L-lysine to accumulate in the fermentation medium or in said coryneform bacteria of step (b); and
 (d) isolating said L-lysine, wherein elimination is achieved by one or more methods of mutagenesis selected from the group consisting of deletion mutagenesis with deletion of two or more codons in the pgi gene; insertional mutagenesis due to homologous recombination; and transition or transversion mutagenesis with incorporation of a non-sense mutation in the pgi gene.

3. A process for increasing the metabolic flux through the pentose phosphate cycle in bacteria of the species *Corynebacterium glutamicum*, said process comprising:
 (a) eliminating the intracellular activity of the endogenous phosphoglucose isomerase (pgi) enzyme in said bacteria; and
 (b) fermenting the bacteria of step (a), wherein elimination is achieved by one or more methods of mutagenesis selected from the group consisting of deletion mutagenesis with deletion of two or more codons in the pgi gene; insertional mutagenesis due to homologous recombination; and transition or transversion mutagenesis with incorporation of a non-sense mutation in the pgi gene.

4. A process for producing L-lysine using bacteria of the species *Corynebacterium glutamicum*, said process comprising:
 (a) eliminating the intracellular activity of the endogenous phosphoglucose isomerase (pgi) enzyme in said bacteria;
 (b) fermenting the bacteria of step (a);
 (c) allowing said L-lysine to accumulate in the fermentation medium or in said bacteria of step (b); and
 (d) isolating L-lysine, wherein elimination is achieved by one or more methods of mutagenesis selected from the group consisting of deletion mutagenesis with deletion of two or more codons in the pgi gene; insertional mutagenesis due to homologous recombination; and transition or transversion mutagenesis with incorporation of a non-sense mutation in the pgi gene.

5. The process of either claim 2 or 4, wherein L-lysine is produced and said coryneform bacteria either overexpress a DNA from *Corynebacterium glutamicum* coding for dihydropicolinate synthase or overexpress a DNA fragment from *Corynebacterium glutamicum* that imparts S-(2-aminoethyl) cysteine resistance.

6. The process of any one of claims 1 to 4 wherein the pgi gene comprises nucleotides 373 to 2022 of the DNA sequence of SEQ ID NO:1.

7. The process of any one of claims 1 to 4 wherein said insertion mutagenesis comprises insertion of the internal fragment of SEQ ID NO:3 into the pgi gene.

8. The process of any one of claims 1 to 4 wherein said insertion mutagenesis comprises insertion of plasmid pMC1 deposited under DSM 12969 into the pgi gene.

* * * * *

SEQUENCE LISTING

<160> NUMBER OF SEQ ID NOS: 12

<210> SEQ ID NO 1
<211> LENGTH: 2811
<212> TYPE: DNA
<213> ORGANISM: Corynebacterium glutamicum
<220> FEATURE:
<221> NAME/KEY: CDS
<222> LOCATION: (373)..(2022)

<400> SEQUENCE: 1

```
aaaacccgag gggcgaaaat tccaccctaa ctttttttggg atcccctttt tccggggaat    60
taattggttt gggtttcaat gggaaaacgg gaaacaatgg gccaaaggtt caaaaacccc   120 aaagggggc cgggttcaaa ttcccaaaaa aaatggcaaa aaaggggggg ccaaaaccaa    180 gttggcccc aaaccaccgg ggcaacggcc cacccacaaa ggggttgggt taaaggaagg    240
acgcccaaag taagcccgga atggcccacg ttcgaaaaag caggccccaa ttaaacgcac   300
cttaaatttg tcgtgtttcc cactttgaac actcttcgat gcgcttggcc acaaaagcaa   360
gctaacctga ag atg tta ttt aac gac aat aaa gga gtt ttc atg gcg gac   411
            Met Leu Phe Asn Asp Asn Lys Gly Val Phe Met Ala Asp
              1               5                  10 att tcg acc acc cag gtt tgg caa gac ctg acc gat cat tac tca aac   459
```

```
                                                      -continued

Ile Ser Thr Thr Gln Val Trp Gln Asp Leu Thr Asp His Tyr Ser Asn
 15              20                  25 ttc cag gca acc act ctg cgt gaa ctt ttc aag gaa gaa aac cgc gcc    507
Phe Gln Ala Thr Thr Leu Arg Glu Leu Phe Lys Glu Glu Asn Arg Ala
 30              35                  40                  45 gag aag tac acc ttc tcc gcg gct ggc ctc cac gtc gac ctg tcg aag    555
Glu Lys Tyr Thr Phe Ser Ala Ala Gly Leu His Val Asp Leu Ser Lys
                 50                  55                  60 aat ctg ctt gac gac gcc acc ctc acc aag ctc ctt gca ctg acc gaa    603
Asn Leu Leu Asp Asp Ala Thr Leu Thr Lys Leu Leu Ala Leu Thr Glu
             65                  70                  75 gaa tct ggc ctt cgc gaa cgc att gac gcg atg ttt gcc ggt gaa cac    651
Glu Ser Gly Leu Arg Glu Arg Ile Asp Ala Met Phe Ala Gly Glu His
         80                  85                  90 ctc aac aac acc gaa gac cgc gct gtc ctc cac acc gcg ctg cgc ctt    699
Leu Asn Asn Thr Glu Asp Arg Ala Val Leu His Thr Ala Leu Arg Leu
     95                  100                 105 cct gcc gaa gct gat ctg tca gta gat ggc caa gat gtt gct gct gat    747
Pro Ala Glu Ala Asp Leu Ser Val Asp Gly Gln Asp Val Ala Ala Asp
110                 115                 120                 125 gtc cac gaa gtt ttg gga cgc atg cgt gac ttc gct act gcg ctg cgc    795
Val His Glu Val Leu Gly Arg Met Arg Asp Phe Ala Thr Ala Leu Arg
                 130                 135                 140 tca ggc aac tgg ttg gga cac acc ggc cac acg atc aag aag atc gtc    843
Ser Gly Asn Trp Leu Gly His Thr Gly His Thr Ile Lys Lys Ile Val
             145                 150                 155 aac att ggt atc ggt ggc tct gac ctc gga cca gcc atg gct acg aag    891
Asn Ile Gly Ile Gly Gly Ser Asp Leu Gly Pro Ala Met Ala Thr Lys
         160                 165                 170 gct ctg cgt gca tac gcg acc gct ggt atc tca gca gaa ttc gtc tcc    939
Ala Leu Arg Ala Tyr Ala Thr Ala Gly Ile Ser Ala Glu Phe Val Ser
175                 180                 185 aac gtc gac cca gca gac ctc gtt tct gtg ttg gaa gac ctc gat gca    987
Asn Val Asp Pro Ala Asp Leu Val Ser Val Leu Glu Asp Leu Asp Ala
190                 195                 200                 205 gaa tcc aca ttg ttc gtg atc gct tcg aaa act ttc acc acc cag gag   1035
Glu Ser Thr Leu Phe Val Ile Ala Ser Lys Thr Phe Thr Thr Gln Glu
                 210                 215                 220 acg ctg tcc aac gct cgt gca gct cgt gct tgg ctg gta gag aag ctc   1083
Thr Leu Ser Asn Ala Arg Ala Ala Arg Ala Trp Leu Val Glu Lys Leu
             225                 230                 235 ggt gaa gag gct gtc gcg aag cac ttc gtc gca gtg tcc acc aat gct   1131
Gly Glu Glu Ala Val Ala Lys His Phe Val Ala Val Ser Thr Asn Ala
         240                 245                 250 gaa aag gtc gca gag ttc ggt atc gac acg gac aac atg ttc ggc ttc   1179
Glu Lys Val Ala Glu Phe Gly Ile Asp Thr Asp Asn Met Phe Gly Phe
255                 260                 265 tgg gac tgg gtc gga ggt cgt tac tcc gtg gac tcc gca gtt ggt ctt   1227
Trp Asp Trp Val Gly Gly Arg Tyr Ser Val Asp Ser Ala Val Gly Leu
270                 275                 280                 285 tcc ctc atg gca gtg atc ggc cct cgc gac ttc atg cgt ttc ctc ggt   1275
Ser Leu Met Ala Val Ile Gly Pro Arg Asp Phe Met Arg Phe Leu Gly
                 290                 295                 300 gga ttc cac gcg atg gat gaa cac ttc cgc acc acc aag ttc gaa gag   1323
Gly Phe His Ala Met Asp Glu His Phe Arg Thr Thr Lys Phe Glu Glu
             305                 310                 315 aac gtt cca atc ttg atg gct ctc ctc ggt gtc tgg tac tcc gat ttc   1371
Asn Val Pro Ile Leu Met Ala Leu Leu Gly Val Trp Tyr Ser Asp Phe
         320                 325                 330
```

-continued

| | |
|---|---|
| tat ggt gca gaa acc cac gct gtc cta cct tat tcc gag gat ctc agc<br>Tyr Gly Ala Glu Thr His Ala Val Leu Pro Tyr Ser Glu Asp Leu Ser<br>335                     340                     345 | 1419 |
| cgt ttt gct gct tac ctc cag cag ctg acc atg gag acc aat ggc aag<br>Arg Phe Ala Ala Tyr Leu Gln Gln Leu Thr Met Glu Thr Asn Gly Lys<br>350                     355                     360                     365 | 1467 |
| tca gtc cac cgc gac ggc tcc cct gtt tcc act ggc act ggc gaa att<br>Ser Val His Arg Asp Gly Ser Pro Val Ser Thr Gly Thr Gly Glu Ile<br>                  370                     375                     380 | 1515 |
| tac tgg ggt gag cct ggc aca aat ggc cag cac gct ttc ttc cag ctg<br>Tyr Trp Gly Glu Pro Gly Thr Asn Gly Gln His Ala Phe Phe Gln Leu<br>               385                     390                     395 | 1563 |
| atc cac cag ggc act cgc ctt gtt cca gct gat ttc att ggt ttc gct<br>Ile His Gln Gly Thr Arg Leu Val Pro Ala Asp Phe Ile Gly Phe Ala<br>            400                     405                     410 | 1611 |
| cgt cca aag cag gat ctt cct gcc ggt gag cgc acc atg cat gac ctt<br>Arg Pro Lys Gln Asp Leu Pro Ala Gly Glu Arg Thr Met His Asp Leu<br>415                     420                     425 | 1659 |
| ttg atg agc aac ttc ttc gca cag acc aag gtt ttg gct ttc ggt aag<br>Leu Met Ser Asn Phe Phe Ala Gln Thr Lys Val Leu Ala Phe Gly Lys<br>430                     435                     440                     445 | 1707 |
| aac gct gaa gag atc gct gcg gaa ggt gtc gca cct gag ctg gtc aac<br>Asn Ala Glu Glu Ile Ala Ala Glu Gly Val Ala Pro Glu Leu Val Asn<br>                  450                     455                     460 | 1755 |
| cac aag gtc gtg cca ggt aat cgc cca acc acc acc att ttg gcg gag<br>His Lys Val Val Pro Gly Asn Arg Pro Thr Thr Thr Ile Leu Ala Glu<br>            465                     470                     475 | 1803 |
| gaa ctt acc cct tct att ctc ggt gcg ttg atc gct ttg tac gaa cac<br>Glu Leu Thr Pro Ser Ile Leu Gly Ala Leu Ile Ala Leu Tyr Glu His<br>            480                     485                     490 | 1851 |
| acc gtg atg gtt cag ggc gtg att tgg gac atc aac tcc ttc gac caa<br>Thr Val Met Val Gln Gly Val Ile Trp Asp Ile Asn Ser Phe Asp Gln<br>495                     500                     505 | 1899 |
| tgg ggt gtt gaa ctg ggc aaa cag cag gca aat gac ctc gct ccg gct<br>Trp Gly Val Glu Leu Gly Lys Gln Gln Ala Asn Asp Leu Ala Pro Ala<br>510                     515                     520                     525 | 1947 |
| gtc tct ggt gaa gag gat gtt gac tcg gga gat tct tcc act gat tca<br>Val Ser Gly Glu Glu Asp Val Asp Ser Gly Asp Ser Ser Thr Asp Ser<br>                  530                     535                     540 | 1995 |
| ctg att aag tgg tac cgc gca aat agg tagtcgcttg cttatagggt<br>Leu Ile Lys Trp Tyr Arg Ala Asn Arg<br>            545                     550 | 2042 |
| cagggcgtg aagaatcctc gcctcatagc actggccgct atcatcctga cctcgttcaa | 2102 |
| tctgcgaaca gctattactg ctttagctcc gctggtttct gagattcggg atgatttagg | 2162 |
| ggttagtgct tctcttattg gtgtgttggg catgatcccg actgctatgt tcgcggttgc | 2222 |
| tgcgtttgcg cttccgtcgt tgaagaggaa gttcactact tcccaactgt tgatgtttgc | 2282 |
| catgctgttg actgctgccg gtcagattat tcgtgtcgct ggacctgctt cgctgttgat | 2342 |
| ggtcggtact gtgttcgcga tgtttgcgat cggagttacc aatgtgttgc ttccgattgc | 2402 |
| tgttagggag tattttccgc gtcacgtcgg tggaatgtcg acaacttatc tggtgtcgtt | 2462 |
| ccagattgtt caggcacttg ctccgacgct tgccgtgccg atttctcagt gggctacaca | 2522 |
| tgtggggttg accggttgga gggtgtcgct cggttcgtgg gcgctgctgg ggttggttgc | 2582 |
| ggcgatttcg tggattccgc tgttgagttt gcagggtgcc agggttgttg cggcgccgtc | 2642 |
| gaaggttttct cttcctgtgt ggaagtcttc ggttggtgtg gggctcgggt tgatgtttgg | 2702 |
| gtttacttcg tttgcgacgt atatcctcat gggttttatg ccgcagatgg taggtgatcc | 2762 |

```
aaagaattca aaaagcttct cgagagtact tctagagcgg ccgcgggcc         2811
```

<210> SEQ ID NO 2
<211> LENGTH: 550
<212> TYPE: PRT
<213> ORGANISM: Corynebacterium glutamicum

<400> SEQUENCE: 2

```
Met Leu Phe Asn Asp Asn Lys Gly Val Phe Met Ala Asp Ile Ser Thr
 1               5                  10                  15

Thr Gln Val Trp Gln Asp Leu Thr Asp His Tyr Ser Asn Phe Gln Ala
            20                  25                  30

Thr Thr Leu Arg Glu Leu Phe Lys Glu Glu Asn Arg Ala Glu Lys Tyr
        35                  40                  45

Thr Phe Ser Ala Ala Gly Leu His Val Asp Leu Ser Lys Asn Leu Leu
    50                  55                  60

Asp Asp Ala Thr Leu Thr Lys Leu Leu Ala Leu Thr Glu Glu Ser Gly
65                  70                  75                  80

Leu Arg Glu Arg Ile Asp Ala Met Phe Ala Gly Glu His Leu Asn Asn
                85                  90                  95

Thr Glu Asp Arg Ala Val Leu His Thr Ala Leu Arg Leu Pro Ala Glu
            100                 105                 110

Ala Asp Leu Ser Val Asp Gly Gln Asp Val Ala Ala Asp Val His Glu
        115                 120                 125

Val Leu Gly Arg Met Arg Asp Phe Ala Thr Ala Leu Arg Ser Gly Asn
130                 135                 140

Trp Leu Gly His Thr Gly His Thr Ile Lys Lys Ile Val Asn Ile Gly
145                 150                 155                 160

Ile Gly Gly Ser Asp Leu Gly Pro Ala Met Ala Thr Lys Ala Leu Arg
                165                 170                 175

Ala Tyr Ala Thr Ala Gly Ile Ser Ala Glu Phe Val Ser Asn Val Asp
            180                 185                 190

Pro Ala Asp Leu Val Ser Val Leu Glu Asp Leu Asp Ala Glu Ser Thr
        195                 200                 205

Leu Phe Val Ile Ala Ser Lys Thr Phe Thr Thr Gln Glu Thr Leu Ser
    210                 215                 220

Asn Ala Arg Ala Ala Arg Ala Trp Leu Val Glu Lys Leu Gly Glu Glu
225                 230                 235                 240

Ala Val Ala Lys His Phe Val Ala Val Ser Thr Asn Ala Glu Lys Val
                245                 250                 255

Ala Glu Phe Gly Ile Asp Thr Asp Asn Met Phe Gly Phe Trp Asp Trp
            260                 265                 270

Val Gly Gly Arg Tyr Ser Val Asp Ser Ala Val Gly Leu Ser Leu Met
        275                 280                 285

Ala Val Ile Gly Pro Arg Asp Phe Met Arg Phe Leu Gly Gly Phe His
    290                 295                 300

Ala Met Asp Glu His Phe Arg Thr Thr Lys Phe Glu Glu Asn Val Pro
305                 310                 315                 320

Ile Leu Met Ala Leu Leu Gly Val Trp Tyr Ser Asp Phe Tyr Gly Ala
                325                 330                 335

Glu Thr His Ala Val Leu Pro Tyr Ser Glu Asp Leu Ser Arg Phe Ala
            340                 345                 350

Ala Tyr Leu Gln Gln Leu Thr Met Glu Thr Asn Gly Lys Ser Val His
        355                 360                 365
```

-continued

```
Arg Asp Gly Ser Pro Val Ser Thr Gly Thr Gly Glu Ile Tyr Trp Gly
    370                 375                 380

Glu Pro Gly Thr Asn Gly Gln His Ala Phe Phe Gln Leu Ile His Gln
385                 390                 395                 400

Gly Thr Arg Leu Val Pro Ala Asp Phe Ile Gly Phe Ala Arg Pro Lys
                405                 410                 415

Gln Asp Leu Pro Ala Gly Glu Arg Thr Met His Asp Leu Leu Met Ser
                420                 425                 430

Asn Phe Phe Ala Gln Thr Lys Val Leu Ala Phe Gly Lys Asn Ala Glu
            435                 440                 445

Glu Ile Ala Ala Glu Gly Val Ala Pro Glu Leu Val Asn His Lys Val
    450                 455                 460

Val Pro Gly Asn Arg Pro Thr Thr Thr Ile Leu Ala Glu Glu Leu Thr
465                 470                 475                 480

Pro Ser Ile Leu Gly Ala Leu Ile Ala Leu Tyr Glu His Thr Val Met
                485                 490                 495

Val Gln Gly Val Ile Trp Asp Ile Asn Ser Phe Asp Gln Trp Gly Val
                500                 505                 510

Glu Leu Gly Lys Gln Gln Ala Asn Asp Leu Ala Pro Ala Val Ser Gly
            515                 520                 525

Glu Glu Asp Val Asp Ser Gly Asp Ser Ser Thr Asp Ser Leu Ile Lys
    530                 535                 540

Trp Tyr Arg Ala Asn Arg
545                 550
```

<210> SEQ ID NO 3
<211> LENGTH: 462
<212> TYPE: DNA
<213> ORGANISM: Corynebacterium glutamicum

<400> SEQUENCE: 3

```
atggagacca atggcaagtc agtccaccgc gacggctccc ctgtttccac tggcactggc        60
gaaatttact ggggtgagcc tggcacaaat ggccagcacg ctttcttcca gctgatccac       120
cagggcactc gccttgttcc agctgatttc attggtttcg ctcgtccaaa gcaggatctt       180
cctgccggtg agcgcaccat gcatgacctt ttgatgagca acttcttcgc acagaccaag       240
gttttggctt tcggtaagaa cgctgaagag atcgctgcgg aaggtgtcgc acctgagctg       300
gtcaaccaca aggtcgtgcc aggtaatcgc ccaaccacca ccattttggc ggaggaactt       360
acccctt cta ttctcggtgc gttgatcgct ttgtacgaac acaccgtgat ggttcagggc       420
gtgatttggg acatcaactc cttcgaccaa tggggcgtgg aa                          462
```

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Universal
      forward primer

<400> SEQUENCE: 4

```
gtaatacgac tcactatagg gc                                                 22
```

<210> SEQ ID NO 5
<211> LENGTH: 19
<212> TYPE: DNA
<213> ORGANISM: Artificial Sequence

```
<220> FEATURE:
<223> OTHER INFORMATION: Description of Artificial Sequence: M13 reverse
      primer

<400> SEQUENCE: 5
ggaaacagct atgaccatg                                                 19

<210> SEQ ID NO 6
<211> LENGTH: 18
<212> TYPE: DNA
<213> ORGANISM: Corynebacterium glutamicum
<220> FEATURE:
<223> OTHER INFORMATION: Internal Primer 1

<400> SEQUENCE: 6
ggaaacaggg gagccgtc                                                  18

<210> SEQ ID NO 7
<211> LENGTH: 18
<212> TYPE: DNA
<213> ORGANISM: Corynebacterium glutamicum
<220> FEATURE:
<223> OTHER INFORMATION: Internal primer 2

<400> SEQUENCE: 7
tgctgagata ccagcggt                                                  18

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: fwd. primer

<400> SEQUENCE: 8
atggarwcca aygghaa                                                   17

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: rev. primer

<400> SEQUENCE: 9
ytccacgccc caytgrtc                                                  18

<210> SEQ ID NO 10
<211> LENGTH: 20
<212> TYPE: DNA
<213> ORGANISM: Corynebacterium glutamicum
<220> FEATURE:
<223> OTHER INFORMATION: Primer pgi-1

<400> SEQUENCE: 10
acccacgctg tcctacctta                                                20

<210> SEQ ID NO 11
<211> LENGTH: 20
<212> TYPE: DNA
<213> ORGANISM: Corynebacterium glutamicum
<220> FEATURE:
<223> OTHER INFORMATION: Primer pgi-2

<400> SEQUENCE: 11
tgtcccaaat cacgccctag                                                20
```

-continued

```
<210> SEQ ID NO 12
<211> LENGTH: 20
<212> TYPE: DNA
<213> ORGANISM: Corynebacterium glutamicum
<220> FEATURE:
<223> OTHER INFORMATION: Primer pgi-2

<400> SEQUENCE: 12
gatgatagcg gccagtgcat                                              20
```